United States Patent [19]

Mauerer et al.

[11] Patent Number: 4,952,205
[45] Date of Patent: Aug. 28, 1990

[54] PRESSURE INFUSION DEVICE

[75] Inventors: Erich Mauerer, Kassel; Reiner Mengel, Niedenstein, both of Fed. Rep. of Germany

[73] Assignee: B. Braun Melsungen AG, Melsungen, Fed. Rep. of Germany

[21] Appl. No.: 427,988

[22] Filed: Oct. 27, 1989

Related U.S. Application Data

[63] Continuation of Ser. No. 173,642, Mar. 25, 1988, abandoned.

[30] Foreign Application Priority Data

Apr. 4, 1987 [EP] European Pat. Off. ............ 87105034

[51] Int. Cl.$^5$ ............................................. A61M 37/00
[52] U.S. Cl. ...................................... 604/67; 604/154; 604/246
[58] Field of Search ................. 604/65, 67, 131, 154, 604/155, 246, 245

[56] References Cited

U.S. PATENT DOCUMENTS 3,701,345 10/1972 Heilman et al. ...................... 604/155
3,720,211  3/1973 Kyrias ................................. 604/155
4,465,475  8/1984 Mardorf et al. ..................... 604/155
4,475,666 10/1984 Bilbrey et al. ....................... 604/155
4,513,796  4/1985 Miller et al. ......................... 604/245
4,560,979 12/1985 Rosskopf ............................ 604/131
4,563,175  1/1986 LaFond .............................. 604/246
4,767,406  8/1988 Wadham et al. ..................... 604/67

FOREIGN PATENT DOCUMENTS 2451197 11/1980 France ............................... 604/155

Primary Examiner—C. Fred Rosenbaum
Assistant Examiner—Denise W. DeFranco
Attorney, Agent, or Firm—Spensley Horn Jubas & Lubitz

[57] ABSTRACT

A pressure infusion device for squeezing out a syringe having an absolute path sensor connected to the movable holder and supplying position data of the position of the syringe rod to a control means. Based on the position data, a motor is controlled so that a desired infusion rate is maintained. The infusion rate may be programmed to vary during an infusion process. Shortly before the empty-state position is reached, an early alarm is released, while, in reaching the empty-state position, the drive is turned off.

11 Claims, 1 Drawing Sheet

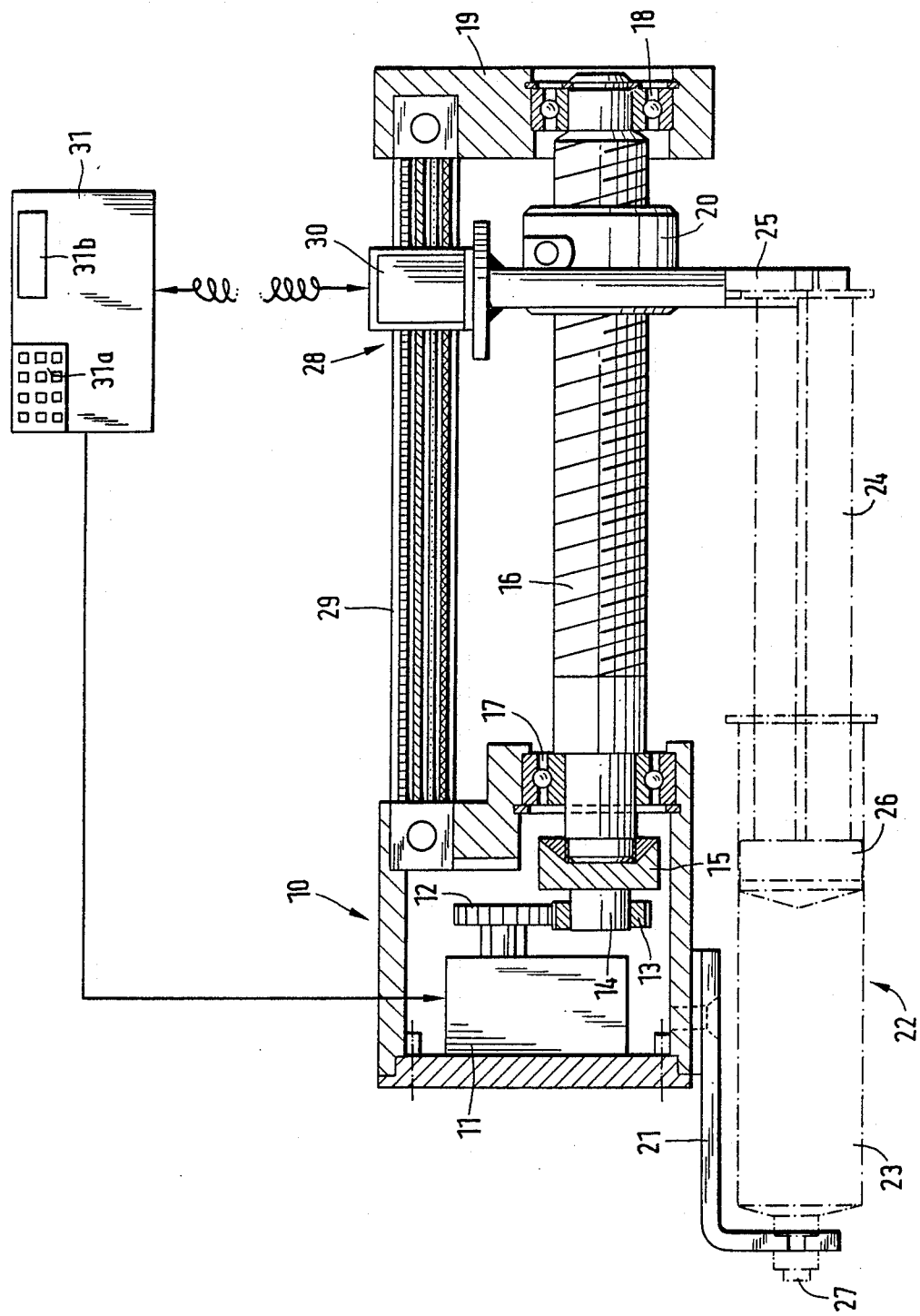

PRESSURE INFUSION DEVICE

This is a continuation of application Ser. No. 07/173,642, filed on Mar. 25, 1988 now abandoned.

BACKGROUND OF THE INVENTION

1. Field of the Invention

The invention relates to a pressure infusion device, and in particular a pressure infusion device for squeezing out a syringe.

2. Description of Related Art

In the case of pressure infusion devices used for carrying out infusions of a liquid into a patient, a syringe containing a liquid is squeezed out continuously, the squeezed out liquid being supplied through a hose to the patient. A known pressure infusion device (U.S. Pat. No. 4,465,475) has an elongated tubular housing to which a first holder is secured for supporting the syringe cylinder. The housing contains a spindle drive and, out of its one end, there extends a slide displaceable along the housing axis and provided with a second holder adapted to be applied to the syringe ram. By rotating a spindle arranged in the housing, the slide is linearly displaced relative to the housing, whereby the syringe mounted in the pressure infusion device is squeezed out. The drive of the advance system is effected by an electric motor.

It has also been known to provide limit switches or early alarm switches at the pressure infusion device. The switches are responsive if a predetermined advance position is reached, so that an alarm is generated or the device is turned off if the syringe is empty or nearly empty. However, an additional expenditure is involved with such limit switches, and, furthermore, a regular check of their perfect functioning is necessary.

The known pressure infusion devices must comply with high precision requirements concerning the advance means and the electric drive, because their total working operation is preset to subsequently take place without being monitored. Therefore, once an infusion rate is set, it must be ensured that the infusion rate is maintained exactly for further operation. In addition, deviations due to manufacturing irregularities and variations in units must not be substantial.

It is an object of the present invention to provide a pressure infusion device in which the total infusion operation is monitored and controlled by ensuring that the infusion conditions are strictly observed.

SUMMARY OF THE INVENTION

In a preferred embodiment of the pressure infusion apparatus of the present invention, the total shift path of the advance means or of the movable holder by which the syringe is squeezed out is monitored by a path sensor. The position data are signaled to the control means, which performs position control in response to a predetermined program or to external measuring data. Thus, the squeezing condition of the syringe is monitored in each stage and signaled to the control means. The control means detects whether the respective position value corresponds to the desired position provided at each moment and makes corrections, if necessary, to temporarily increase or decrease the advance speed. Therefore, it is possible to change, in a time-controlled or quantity-controlled manner, the infusion rate in accordance with a schedule by first setting, for instance, a high infusion rate which will be subsequently reduced continuously. On the other hand, the advance may be also controlled in response to external measuring data which, for instance, are conclusive as to the effect of the infused medication. If a hypotensive preparation is administered, the infusion rate may be varied subject to the instantaneous blood pressure of the patient.

It is a particular advantage of the present invention that not only specific infusion rates may be preset, but also that adherence to said infusion rates may be monitored exactly and signaled to the control means. Probable deviations may be compensated by using known control criteria.

Preferably, the path sensor is of the absolute value type, which, with respect to a fixed reference position, detects the position of a second holder moving the syringe rod. Since the respective absolute position of the second holder is detected, and the empty-state position of the second holder (in which the syringe is completely squeezed out) is a predetermined position, no limit switches are required for generating an early alarm or for the limit disconnection of the drive. The empty-state position for each syringe type may be input manually into an input means of the control means. Further, the empty-state position may be input in that the syringe is mounted in empty condition into the pressure infusion device. By depressing a push-button, the respective position of the second holder may be stored in the control means. Subsequently, the syringe may be charged in that the piston is withdrawn in the cylinder. The resultant position of the second holder provides information (with due regard to the syringe cross section) about the liquid volume charged by the syringe.

Further, the control means may monitor the syringe to detect blocking of the infusion operation. If the tube adapted to the syringe is, for instance, bent, and a further advance is inhibited (although the empty-state position has not yet been reached), this may be detected in that the syringe advance is slower than a predetermined value, thus requiring the release of an alarm. Hence, for detecting a blocking of the infusion, it is not necessary to provide load measuring means.

DESCRIPTION OF THE PREFERRED EMBODIMENT

With reference to one sole FIGURE of the drawing, an embodiment of the invention will be explained hereunder in more detail.

The drawing shows a schematic longitudinal section of a pressure infusion device.

Said pressure infusion device comprises a housing 10 accommodating a motor-gear unit 11 which drives, via gears 12 and 13, a shaft 14 that, through coupling 15, is connected to one end of the threaded spindle 16. In the vicinity of said end, said threaded spindle 16 is supported by a bearing 17 in the wall of housing 10. The threaded spindle 16 projects out of the housing 10, and its opposite end is positioned with a bearing 18 in a block 19 which, via a (non-illustrated) bridge is integrated with housing 10. On the threaded spindle 16, a slide 20 in the form of a spindle nut is guided. Its inner thread engages the external thread of the threaded spindle 16. Said slide 20 is retained against rotation so that, in the case of a rotation of the threaded spindle 16, it moves in the longitudinal direction of the threaded spindle. Elements 11 to 20 comprise a preferred embodiment of the advance means which, alternatively, may be also designed like that of the pressure infusion device according to U.S. Pat. No. 4,465,475.

To the housing 10, the first holder 21 is fixed in which the neck of the syringe cylinder 23 of syringe 22 provided. The end of the syringe rod 24 is placed into the second holder 25, which is integrally connected to the slide 20. In the syringe cylinder 23, the syringe 22 contains a piston 26 joined firmly to the rod 24 and expelling the fluid contained in the syringe out of the outlet 27, to which a tube may be connected.

According to a preferred embodiment of the invention, a path sensor 28 is provided to detect the axial position of the slide 20 with respect to the housing 10 or with respect to the first holder 21. The path sensor 28 comprises an encoded rail 29 extending between housing 10 and block 19, as well as a scanning head 30 movable along rail 29 and integrally connected to the second holder 25. The scanning head 30 is provided with a plurality of sensors, with each sensor being adapted to be moved along a signal track of the signal rail 29. The signal rail 29 comprises signal tracks which may be scanned magnetically or optically. From the combination of the signals of the sensors contained in scanning head 30, information may be obtained about the position of the scanning head 30 in the longitudinal direction of the signal rail 29. As for details, the model 500 position sensor manufactured by the MITUTOYO company may be used as the position sensor 28. The resolution of such a position sensor is approximately 0.01 mm.

The output signals of the scanning head 30, which represent the position signals of the second holder 25, are supplied to the control means 31. The control means 31 accommodates a microprocessor which, responsive to the position signals, controls the motor of the motor-gear unit 11. By a keyboard 31a of the control means 31, various parameters of the infusion operation may be input into the microprocessor, such as, for instance the inner cross section of the syringe cylinder 23, the liquid volume contained in the syringe and the empty-state position of the syringe (i.e., the position occupied by holder 25 if the syringe is completely squeezed out). Moreover, the desired infusion rate, namely the liquid volume to be squeezed out per time unit, may be input. It is also possible to input a number of different infusion rates which shall become effective successively during one and the same infusion process. From the inputted data, the microprocessor calculates the respective infusion rate. By timing, it is detected whether the respective actual infusion rate corresponds to the desired one. The speed of the motor is corrected responsive to the resultant deviation.

The control performed by the device 31 may be carried out either by means of the path data inputted and supplied by the scanning head 28, or by means of the volume data which form the product of path and cross sectional surface of the syringe cylinder 23.

The display means 31b of the control means 31 may indicate the fluid volume already squeezed out of the syringe, or the fluid volume still contained in it. Further, the still available infusion time may be displayed.

The empty-state position occupied by scanning head 30 or by the second holder 25 if the syringe 22 is completely squeezed out may be either input manually by keyboard 31a, or it may be input in that an empty syringe not containing any fluid, is inserted with advanced piston into holders 21 and 25. The position taken by the holder 25 in such a condition is stored in the control means 31 by depressing a respective key. Subsequently, the pressure infusion device may be used to charge liquid into the syringe 22 in that the slide 20 withdraws rod 24. Upon termination of the charging process, the position value of the scanning head 30 is also stored in the control means 31. Thus, the control means contains instructions about the volume of the charged liquid in the syringe.

On the other hand, it is possible to use and squeeze out under control a syringe of known dimensions which are stored in the control means 31.

Upon reaching a position which, by a specific distance, is in advance of the empty state position of the syringe, an alarm is released by the control means 31 to alert the staff that the infusion process will be shortly terminated so that, if necessary, a new syringe may be applied. The position in which the early alarm is released may be so selected that a specific residual infusion time is left. In such a case, the position at which early alarm is triggered, varies subject to the advance speed.

Moreover, device 31 controls that the advance speed or the infusion rate do not fall short of a predetermined minimum value. If the latter is not reached (for instance because the tube connected to the syringe 22 is kinked or closed for other reasons), the control means detects the insufficient minimum speed and an alarm is released.

One sole control means may be operated in connection with a plurality of pressure infusion devices of which each contains a path sensor 28. It is possible in this way to intercoordinate the pressure infusion devices. This is suitable if a number of infusions must be administered simultaneously and in specific amount ratios to a patient. If a pressure infusion device does not work properly, all pressure infusion devices may be turned off. But it is also possible to operate them such that by adhering exactly to a specific, predetermined ratio of amounts, the infusion solutions are administered to the patient. One of several pressure infusion devices may be also used as a master unit while the remaining devices, in accordance with the path signals generated by the path sensor of the master unit, may serve as follow-up units.

Due to the pressure infusion device of the present invention, even the smallest amounts of liquid may be very precisely dosed and applied from an optionally high volume. The accuracy requirements concerning the advance means and the drive are very moderate because the high accuracy of the system is obtained by the path sensor.

What is claimed is:

1. A pressure infusion device for squeezing out a syringe, comprising:
    a holder for supporting the syringe,
    an advance means for squeezing out the syringe,
    a path sensor for detecting the position of the advance means over the total range of motion of the advance means and for generating a signal in response thereto,
    control means responsive to the path sensor signal for controlling movement of the advance means in response to a prestored program or to external measuring data,
    input means for inputting into the control means an empty state signal corresponding to the signal generated by the path sensor when the syringe is fully squeezed out, and
    alarm means for releasing an alarm when the advance means reaches an alarm position, the alarm position being in advance of the empty state position of the syringe.

2. A pressure inflation device as defined in claim 1, further comprising:
a syringe rod,
a holder for moving the syringe rod, wherein said path sensor further includes
detection means for detecting the position of the holder for moving the syringe rod with respect to a fixed reference position.

3. A pressure infusion device as defined in claim 1 wherein said input means further comprises
push button means for inputting into the control means an empty state signal corresponding to the signal generated by the path sensor when the syringe is fully squeezed out.

4. A pressure infusion device as defined in claim 1, further comprising:
calculation means for calculating the difference between the position of the advance means and the position of the advance means when the syringe is fully squeezed out, and
alarm means responsive to said calculation means for releasing an alarm if said difference falls below a predetermined value.

5. A pressure infusion device as defined in claim 1, further comprising:
conversion means for converting the position of the advance means into the fluid volume based on inputted parameters of the syringe.

6. A pressure infusion device as defined in claim 6, further comprising:
display means for indicating the volume of liquid squeezed out of the syringe.

7. A pressure infusion device as defined in claim 1, further comprising:
detection means for detecting whether the advance means has moved a predetermined minimum distance within a predetermined period of time, and
alarm means responsive to said detection means for releasing an alarm if said advance means has not moved said predetermined minimum distance within said predetermined period of time.

8. A pressure infusion device as defined in claim 1, further comprising:
a plurality of syringes,
a corresponding plurality of advance means for squeezing out the syringes, each of said advance means having a corresponding path sensor,
said control means being operable to simultaneously control movement of each of said plurality of advance means.

9. A pressure infusion device as defined in claim 5, further comprising:
display means for indicating the volume of liquid contained in the syringe.

10. A device as in claim 1 wherein the alarm position and the empty state position are spaced apart by a predetermined residual infusion distance.

11. A device as in claim 1 wherein the release of the alarm and the input of the empty state signal are spaced apart by a predetermined residual infusion time interval.

* * * * *